United States Patent [19]

Sheehan et al.

[11] 4,265,882

[45] May 5, 1981

[54] SULPHUR ANALOGS OF PENICILLINS HAVING A NUCLEOPHILE SUBSTITUTED IN THE 6 AND 7 POSITION, RESPECTIVELY

[75] Inventors: John C. Sheehan, Lexington; Thomas J. Commons, Boston, both of Mass.

[73] Assignee: Massachusetts Institute of Technology, Cambridge, Mass.

[21] Appl. No.: 838,874

[22] Filed: Oct. 3, 1977

[51] Int. Cl.$^3$ .......................................... C07D 499/00
[52] U.S. Cl. .................................. 424/114; 424/271; 424/246; 260/245.2 R
[58] Field of Search ..................... 260/306.7 C, 245.2; 424/271, 114, 246

[56] References Cited

U.S. PATENT DOCUMENTS

| | | | |
|---|---|---|---|
| 3,159,617 | 12/1964 | Sheehan | 260/239.1 |
| 3,206,469 | 9/1965 | Pifferi | 260/306.7 C |
| 3,868,365 | 2/1975 | Dolfini et al. | 260/239.1 TB |
| 3,880,837 | 4/1975 | Lunn | 260/306.7 C |
| 4,020,077 | 4/1977 | Cook et al. | 260/306.7 C |
| 4,033,979 | 7/1977 | Bentley et al. | 260/306.7 C |
| 4,061,629 | 12/1977 | Dolfini et al. | 260/239.1 TB |
| 4,062,842 | 12/1977 | Dolfini et al. | 260/239.1 TB |
| 4,093,625 | 6/1978 | Commons et al. | 424/270 |

OTHER PUBLICATIONS

Barton et al., Proc. R. Soc. Lond. B 179 345(1971).
Gutowski, Tet. Lett. 1779 (1970).
Riner et al., Helv. Chim. Acta 51 1905(1968).
Hauser et al., Helv. Chim. Acta 50 1327(1967).
Morin et al., Chem. of Cephalosporin Antibiotics, Progress in the Chemistry of Organic Natural Products XXVIII (1970).
Cama et al., JACS 94 1408(1972).
Spitzer et al., Tet. Letter No. 4 273(1973).
Flynn, Cephalosporins and Penicillins, Chapter 15 Academic Press (1972).
Jen et al., J. Or. Chem. 38, 2857(1973).
Slusarchyk et al., J. Org. Chem. 38, 943(1973).
Gutowski, et al., Tet. Lett. (1971) 3429, 3433.

*Primary Examiner*—Nicholas S. Rizzo
*Attorney, Agent, or Firm*—Arthur A. Smith, Jr.; George W. Neuner

[57] ABSTRACT

Biologically active sulfur analogs of 6-aminopenicillanic acid having a nucleophile substituted in the 6-position are made by reacting a sulfenyl chloride with esters of diazopenicillanic acid. Biologically active sulfur analogs of 7-aminocephalosporanic acid having a nucleophile substituted in the 7-position are analogously made by reacting a sulfenyl chloride with esters of 7-diazocephalosporanic acid. Deacetoxycephalosporins can be formed from the corresponding analog of 6-aminopenicillanic acid and derivations thereof, by sulfoxide rearrangement of the thiazolidine ring of penicillins to the dihydrothiazine ring of cephalosporins. These nucleophile substituted sulfur analogs of penicillins and cephalosporins are new antibacterial agents and display antibacterial activity against a variety of microorganisms.

28 Claims, No Drawings

SULPHUR ANALOGS OF PENICILLINS HAVING A NUCLEOPHILE SUBSTITUTED IN THE 6 AND 7 POSITION, RESPECTIVELY

FIELD OF THE INVENTION

This invention relates to derivatives of penicillins and cephalosporins, and particularly to sulfur analogs of 6-aminopenicillanic acid and 7-aminocephalosporanic acid that have nucleophile substituents in the 6 and 7 position, respectively.

BACKGROUND OF THE INVENTION

In U.S. Pat. No. 3,159,617, there is taught the first commercial syntheses of 6$\beta$-aminopenicillanic acid and penicillin derivatives based thereon. A vast number of derivatives of the 6$\beta$-aminopenicillanic acid may be formed by introduction of various groups into the amino group of the acid. Thus, acyl groups, isocyanates, isothiocyanates, halogen compounds, methylisoureas, ethylene oxide, ethylene imine, and the like have been introduced into the amino group of 6$\beta$-aminopenicillanic acid to form both biologically active and biologically inactive derivatives.

Many of the derivatives of 6$\beta$-aminopenicillanic acid, especially those derivatives formed by acylation, have become useful drugs. For example, ampicillin and carbenicillin have broadened the spectra to activity to include use against certain Gram-negative organisms while methicillin shows good activity against certain resistant staphylococci.

In an effort to find new biologically active derivatives of 6$\beta$-aminopenicillanic acid, attempts have been made to modify the parent compounds by myriad methods, in addition to the mere functionalization of the amino group. Thus, stimulated by the eluciadation of the structure of the cephalosporins, there have been attempted modifications of the thiazolidine moiety of 6$\beta$-aminopenicillanic acid. This transformation is particularly useful since cephalosporins are not readily available from nature. Thus, much effort has been concentrated on the investigation of possible transformations of the thiazolidine ring to the dihydrothiazine ring without any concomitant change of the chemically sensitive $\beta$-lactam moiety. These efforts are described by D. H. R. Barton and T. G. Sammes, *Proc. R. Soc. Lond. B*, 179 345 (1971).

Other attempts have been made to modify 6$\beta$-aminopenicillanic acid through reaction of the $\beta$-lactam moiety, but such attempts are relatively few and are focused on variation of the substituents or sterochemistry of the C-6 carbon in the penam system. Primarily, four types of modifying reactions are reported, namely acylation, epimerization, alkylation and diazotization.

One successful example of the epimerization reaction is reported by G. E. Gutowski, *Tet. Lett.*, (1970), 1779 and 1863. However, this penicillin having the epimerized C-6 substituent is devoid of any biological activity. With regard to alkylation at the C-6 position, most attempts, based upon earlier predictions that the introduction of an $\alpha$-methyl group at the C-6 position might enhance antibiotic activity, have been directed to such introduction. Further, both direct and indirect $\alpha$-hydroxylalkylation of the penicillin nucleus at C-6 with benzaldehyde and formaldehyde has been reported by R. Riner and P. Zeller, *Helv Chim. Acta,* 51, 1905 (1968). These derivatives and other $\alpha$-alkylated derivatives show some biological activity, but both display substantially less activity than the well known penicillin G.

Deamination of $\beta$-aminopenicillanic acid by sodium nitrite in mineral acid proceeds with inversion at C-6, resulting in the C-5 and C-6 protons being trans-oriented in the product. Moreover, when the reaction is run in the presence of a haloacid, a 6$\alpha$-halo product is obtained. Deamination of 6$\beta$-aminopenicillanic acid by sodium nitrite with oxy acids is reported by T. Hauser and H. P. Sigg, *Helv. Chim Acta,* 50, 1327, (1967). With such oxy acids, 6$\alpha$-hydroxypenicillanic acid is isolated as the benzyl ester and is readily transformed to the $\alpha$-oxygen analog of penicillin V, 6$\alpha$-phenoxyacetoxypenicillanic acid. This material also exhibits no biological activity.

Similar chemical transformations and derivatizations in the cephalosporin antibiotic series are reported in part by R. B. Morin and B. G. Jackson, "Chemistry of Cephalosporin Antibiotics", Progress in the Chemistry of Organic Natural Products XXVIII, Wein, Springer-Verlag (1970).

A naturally occurring cephalosporanic derivative containing an $\alpha$-methoxy group in the 7- position was isolated from *Streptomyces lipmanii* NRRL 3584 and reported by Higgens and Kastner, (1971) and by Nagarajan et al., (1971) to have exhibited greater activity than Cephalosporin C against gram-negative microorganisms (See Edwin H. Flynn, "Cephalosporins and Penicillins: Chemistry and Biology", Chapter 15, Academic Press, New York and London (1972). Cama et al. describe the stereospecific introduction of a methoxy group at the C-6(7) position of derivatives of naturally occurring penicillin and cephalosporin compounds in "Substituted Penicillin and Cephalosporin Derivatives. I. Stereospecific Introduction of the C-6(7) Methoxy Group", *J. Amer. Chem. Soc.,* 94 1408 (1972).

Further, three new series of these penicillins and cephalosporins have recently been described in copending U.S. Patent Appln. Ser. No. 347,772, filed Apr. 3, 1973; U.S. Patent Appln. Ser. No. 494,507, filed Aug. 5, 1974; U.S. Patent Appln. Ser. No. 616,979, filed Sept. 26, 1975; and U.S. Patent Appln. Ser. No. 712,540, filed Aug. 9, 1976. These series, the carbon, oxygen and sulfur analogs of penicillins and cephalosporins, are characterized by the replacement of the 6-nitrogen of the "normal" antibiotic with carbon, oxygen or sulfur, respectively. These novel analogs and the wide variety of derivatives obtainable therefrom are biologically active and provide new series of antibiotics.

For brevity, the commonly accepted abbreviations of 6-APA for 6$\beta$-aminopenicillanic acid, 6-SPA for the sulfur analogs thereof, 7-ACA for 7$\beta$-aminocephalosporanic acid and 7-SCA for the sulfur analogs thereof will be used throughout the specification.

SUMMARY OF THE INVENTION

The present invention provides new classes of penicillins and cephalosporins that are sulfur analogs of 6-aminopenicillanic acid (6-APA; sulfur analog, 6-SPA) or 7-aminocephalosporanic acid (7-ACA; sulfur analog, 7-SCA) having nucleophiles substituted at the 6- or 7-position, respectively. Some of these new compounds have been found biologically active against a variety of microorganisms. Preferably these nucleophiles are substituted in the 6$\alpha$- or 7$\alpha$-positions.

The invention also provides methods for making such sulfur analogs of 6-APA and 7-ACA, (6-SPA and 7-SCA, respectively) having nucleophiles substituted at the 6- or 7-position, respectively. One method comprises treating the diazo ester of 6-APA or 7-ACA with a sulfenyl halide either by itself or in the presence of a nucleophile. As used herein, the term "nucleophile" refers to a group of compounds that is electron rich and has an unshared pair of electrons that acts as a reactive site. Examples of such nucleophiles include halogens, alcohols, acids, esters, amines, amides, thiols, sulfides, and the like.

DESCRIPTION OF THE INVENTION AND PREFERRED EMBODIMENT

The employment of esters of 6-diazopenicillanic acid and 7-diazocephalosporanic acid as sources of novel antibacterial agents, particularly sulfur analogs of 6-APA and 7-ACA, 6-SPA and 7-SCA, respectively has been described in copending U.S. Patent Appl. Ser. No. 712,540, described above, which is hereby incorporated by reference.

We have now found that esters of 6-APA and 7-ACA compounds can be treated with sulfenyl halides to form 6-SPA and 7-SCA compounds, respectively, with nucleophiles in the 6- and 7-position, respectively. Because of the stereochemistry of these $\beta$-lactam ring compounds, the nucleophiles are generally substituted in the $\alpha$-position. These new compounds generally have a structural formula

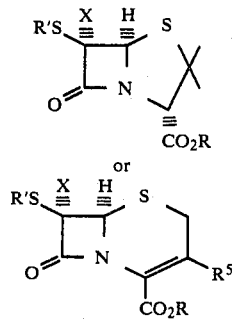

wherein R is a protective group for acids, $R^1$ is hydrogen or an organic moiety that is electrophilic with respect to the sulfur to which it is attached, $R^5$ is a pharmaceutically acceptable group and X is a nucleophile.

Protective groups for acids are well-known and are described, for example, in J. F. W. McOmie, *Protective Groups in Organic Chemistry* (Plenum Press, 1973), particularly in Chapter 7, p. 183 et. seq., "Protection of Carboxyl Groups" by E. Haslam. Typical examples of such protective groups include, for instance, (1) substituted or unsubstituted aliphatic, alicyclic or aromatic groups, e.g. alkyl groups (preferably lower alkyl groups such as methyl, ethyl, propyl, t-butyl, $\beta\beta\beta$-trichloroethyl, etc.), cycloalkyl groups (e.g. cyclohexyl), aryl groups (e.g. phenyl, tolyl), aralkyl groups (e.g. benzyl, methylbenzyl, p-nitrobenzyl, 9-anthrylmethyl, etc.), or alkaryl groups; (2) substituted or unsubstituted phenacyl groups, e.g. phenacyl, p-methoxy phenacyl, m-chlorophenacyl; (3) salts including alkali metal salts such as sodium or potassium salts, as well as quaternary ammonium groups such as N-ethyl piperidino and dicyclohexylamino; or (4) organo silyl groups, e.g. alkyl silyls such as trimethyl silyl, triethyl silyl, etc. Most preferred at present are lower alkyl, particularly t-butyl, halogenated lower alkyl, particularly $\beta\beta\beta$-trichloroethyl, phenacyl, benzhydryl, benzyl, and trimethylsilyl groups.

A variety of organic moieties are useful for substituent $R^1$, including, for example, substituted or unsubstituted aliphatic moieties, such as alkyl moieties, preferably lower alkyl moieties, including methyl, ethyl, propyl, hexyl moieties, etc; alicyclic moieties, such as cycloalkyl moieties, including cyclopentyl, cyclohexyl, methylcyclohexyl moieties, etc.; aromatic moieties, such as phenyl, benzyl, tolyl moieties, etc.; acyl moieties, such as benzoyl, phenoxyacetyl, chloroacetyl and bromoacetyl moieties, etc.; carboxylic moieties; carbonic moieties; sulfonic moieties; and amide moieties. Groups that are bound to the sulfur atom by a carbonyl group are preferred for $R^1$. Examples of useful $R^1$ substituents include hydrogen, formyl, acetyl, phenyl, phenylacetyl, phenoxyacetyl, p-aminophenylacetyl, $\alpha$-carboxylphenylacetyl, benzyl, benzoyl, 2-thienylacetyl, aminocarbamyl, phenylglycyl, methyl sulfonyl, benzyl sulfonyl, o-aminophenylsulfonyl, p-aminobenzylsulfonyl, carbobenzoxy, $\alpha$-carbonaphthoxy, carbo(2-thienylmethoxy), (1-phenyl2-formylamino)ethoxycabonyl, and $\beta$, $\beta$, $\beta$-trichloroethoxycarbonyl.

$R^5$ can be any of a wide variety of groups that are well-known in the cephalosporin art. Commonly $R^5$ is a methyl or methylacetoxy group, however, a wide variety of pharmaceutically acceptable groups can be substituted for $R^5$ by reactions well-known to those skilled in the art.

Nucleophiles useful for the substituent X in this invention include halogen and organic nucleophiles such as alcohols, acids, esters, amines, amides, sulfides, and the like, etc. Preferred nucleophiles are halogen and alkoxy moieties, particularly lower alkoxy moieties having from 1 to about 6 carbon atoms.

Removal of the acid protective group, R, from the above compounds produces the free acids,

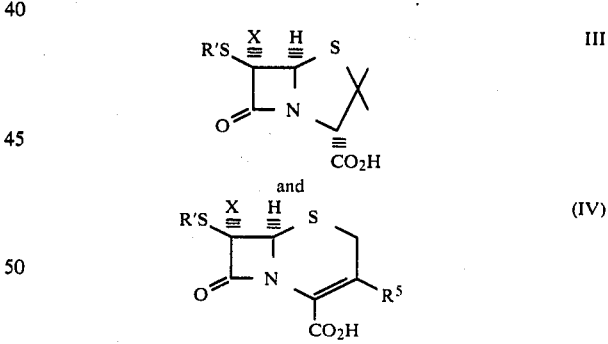

where $R^1$, $R^5$ and X are the same as described above. While it should be understood that some of the aforesaid acid protective groups may be more difficult to remove than others, these groups have heretofore been used as protective groups in analogous penicillins and cephalosporins and the carbon and oxygen analogs thereof. Removal of such groups is effected in accordance with well-recognized procedures, dependent upon the identity of the group. See McOmie, *Protective Groups In Organic Chemistry, supra.*

These free acids, exhibiting a reactivity similar to 6-APA, 6-SPA, 7-ACA, and 7-SCA, may be esterified to penicillanates and cephalosporanates of the general formulas:

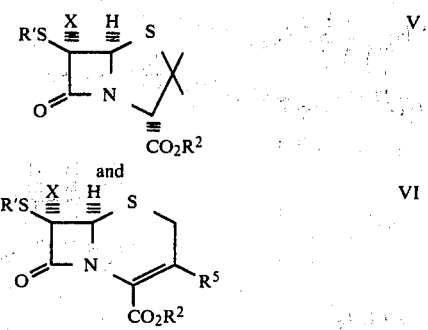

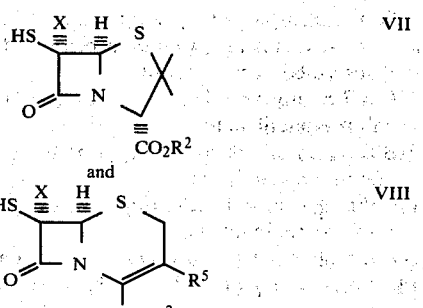

where $R^1$, $R^5$ and X are the same as described above, and $R^2$ represents pharmaceutically acceptable groups, as well known in the art. $R^2$ may be selected from any of the groups from which R may be selected, as described above, namely, either R or $R^2$ may be hydrogen or substituted or unsubstituted (1) aliphatic, alicyclic or aromatic groups, e.g. alkyl groups, preferably lower alkyl groups such as methyl, ethyl or propyl; alkenyl groups, preferably lower alkenyl groups, such as ethenyl, propenyl and butenyl; alkinyl groups, preferably lower alkinyl groups such as ethinyl, propinyl and butinyl; cycloalkyl or cycloalkenyl groups, such as cyclohexyl; aralkyl such as benzyl and phenylethyl; (2) acyl groups, including acylalkyl groups, preferably lower acylalkyl groups such as acetylmethyl, acetylethyl, and acetylpropyl; acylamino groups, preferably lower acylamino groups, such as acetylamino, propionylamino, and butyrylamino; acylaminoalkyl groups, preferably lower acylaminoalkyl groups, such as acetylaminomethyl, acetylaminoethyl; imino groups (see U.S. Pat. No. 3,876,630 issued April 8, 1975 to Ishimara et al), and arylacyl groups such as the phenylacyl group and its derivatives previously mentioned in connection with R; (3) salt formers, e.g. alkali metal ions, or organic ammonium groups such as tri(alkyl)ammonium groups (preferably tri(lower alkyl)ammonium groups, e.g. triethylammonium; or piperidino groups or N-alkyl(preferably lower alkyl)piperidino groups, or benzylammonium groups; and (4) organo silyl groups, preferably tri(lower alkyl)silyls.

$R^1$ may be appropriately selected so as to adduce facile cleavage of the $R^1$-S bond. Such cleavage results in the parent series of sulfur analogs having the following general formulas:

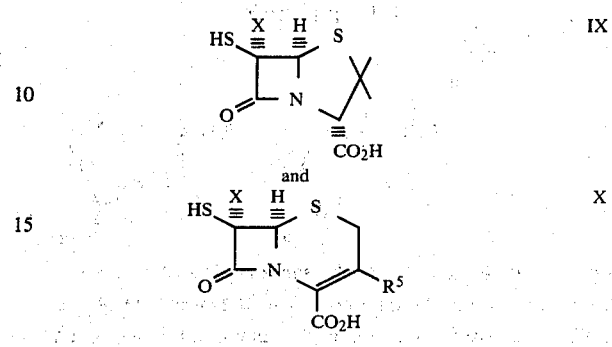

where $R^2$, $R^5$ and X are the same as described above.

Substituents useful in such cleavage reaction are characterized by $R^1$ being a good leaving group, e.g. good electron withdrawing groups. These include chloroacetyl, bromoacetyl, ethoxyacetyl, nitrobenzoyl, dimethoxylmethyl, $\beta,\beta,\beta$-trichloroethoxycarbonyl, and substituted and unsubstituted phenoxyacetyl groups.

These thiol compounds, of course, on removal of the pharmaceutically acceptable group $R^2$ as discussed above with respect to R, afford the parent compounds

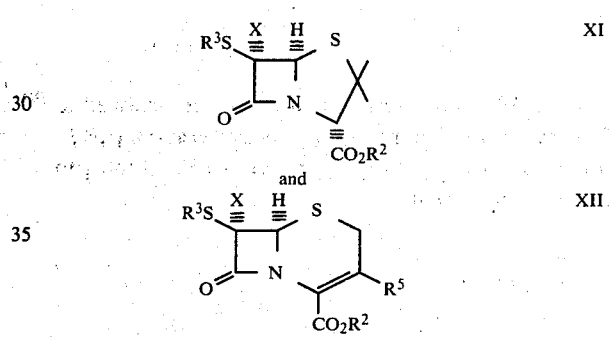

where $R^5$ and X is the same as described above.

This parent moiety is readily functionalized at the $6\beta$ and $7\beta$ position, and/or esterified on the acid substituent to produce sulfur analogs of the general formula as follows:

where $R^2$, $R^5$ and X are the same as described above and $R^3$ is an organic electrophile similar to those well-known in penicillin and cephalosporin side chain technology. Preferably, $R^3$ is selected from the same substituents given above for $R^1$. Thus after introduction of sulfur at the 6 position in the penicillanic compounds, both the substituent $R^1$ (or $R^3$) attached to the sulfur, and the substituent R (or $R^2$) on the 3-carboxylic acid ester can be changed by reactions of which those skilled in the art will be well aware. With regard to the cephalosporanic compounds, the corresponding R (or $R^2$) and $R^1$ (or $R^3$) can similarly be varied. Further, the X substituent can also be varied through reactions well-known in the analogous arts.

The synthetic approach to these two antibiotic series, characterized by a sulfur atom at the $6\beta$ and $7\beta$ positions involves first the synthesis of the appropriate esters, 6-diazopenicillanate and 7-diazocephalosporanate, respectively. An example of such a synthetic scheme is described in J. C. Sheehan, Y. S. Lo, J. Loliger and C. C. Podewell, *J. Org. Chem.*, 39 1444 (1974), which involves the diazotization of the corresponding penicillin or cephalosporin with dinitrogen tetroxide and treatment of the resultant nitroso derivative with silica gel or a base in a refluxing organic solvent.

The 6-diazopenicillanate is then treated with a sulfenyl halide either by itself or in the presence of a halogen or an organic nucleophile according to the following reaction where a sulfenyl chloride is used for illustration.

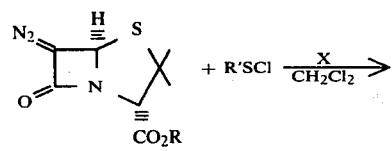

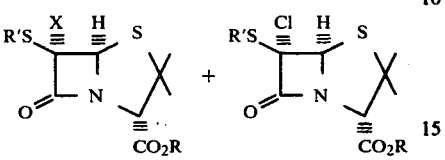

wherein R, $R^1$ and X are the same as described above. The reaction can be carried out in the presence of the sulfenyl chloride without any organic nucleophile as follows:

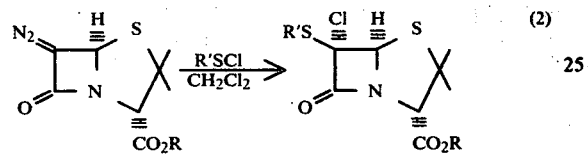

When $R^1$ is a carbonyl group, it may be removed to form the corresponding mercaptan. For example $\beta,\beta,\beta$-trichloroethyoxycarbonyl can be removed according to the following reaction:

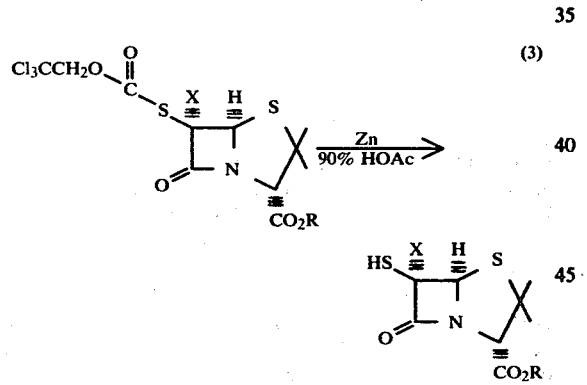

wherein R and X are the same as described above.

7-Diazocephalosporanate may be treated similarly to 6-diazopenicillanate as illustrated above resulting in the following reactions:

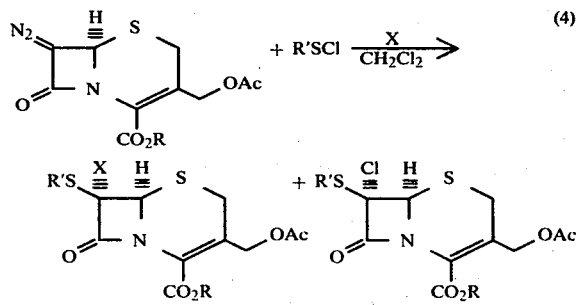

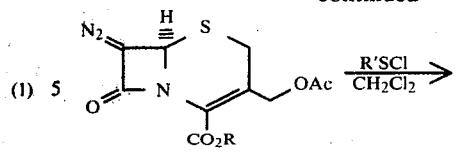

The deacetoxycephalosporins of this invention may be formed from the corresponding analog of 6-SPA and derivatives thereof, by sulfoxide rearrangement of the thiazolidine ring of penicillins to the dihydrothiazine ring of cephalosporins, for example, in accordance with the following reaction:

Some examples of penicillins and cephalosporins in accord with this invention and produced by the methods described herein include:

$\beta,\beta,\beta$-Trichloroethyl 6$\beta$-(methoxycabothio)-6$\alpha$-chloropenicillanate $\beta,\beta,\beta$-Trichloroethyl 6$\beta$-(methoxycarbothio)-6$\alpha$-methoxypenicillanate Benzhydryl 6$\beta$-($\beta,\beta,\beta$-Trichloroethoxycarbothio)-6$\alpha$-methoxypenicillanate Benzhydryl 6$\beta$-mercapto-6$\alpha$-methoxypenicillanate Benzhydryl 6$\beta$-(phenylacetylthio)-6$\alpha$-methoxypenicillanate benzhydryl 6$\beta$-($\beta,\beta,\beta$-trichloroethoxycarbothio)-6$\alpha$-chloropenicillanate Benzhydryl 6$\beta$-(thiophene-2-acetylthio)-6$\alpha$-methoxypenicillanate t-Butyl 7$\beta$-(methoxycarbothio)-7$\alpha$-methoxycephalosporanate t-Butyl 7β-(β,β,β-trichloroethoxycarbothio)-7β-methoxycephalosporanate t-Butyl 7β-mercapto-7α-methoxycephalosporanate t-Butyl 7β-(phenoxyacetylthio)-7α-methoxycephalosporanate t-Butyl 7β-(phenylacetylthio)-7α-methoxycephalosporanate t-Butyl 7β-(thiophene-2-acetylthio)-7α-methoxycephalosporanate β,β,β-Trichloroethyl 7β-(methoxycarbothio)-7α-methoxydeacetoxycephalosporanate t-Butyl 7β-(β,β,β-trichloroethoxycarbothio)-7α-chlorocephalosporanate The antibiotic compounds or antibiotic derivations of compounds of the present invention may be administered to mammals in essentially the same ways the previously known penicillin- and cephalosporin-based antibiotics are administered. They can be administered to mammals, e.g. humans, dogs, mice, rats, etc., orally, parenterally, rectally, or topically (e.g. for treatment of skin infections). Common dosages for oral administration, for example, range from about 1 to 200 mg/kg/day, in divided dosages. The compounds can be administered as such or in the form of pharmacologically acceptable salts, and may be admixed with carriers or adjuvants or both. In such preparations the ratio of the therapeuric substance and the carriers and adjuvants may vary from about 1% to 99%.

The preparations may either be produced as for instance, tablets, pills or suppositories, or can be supplied in medical containers, such as capsules, or as regards mixtures, they can be filled in bottles. Pharmaceutically acceptable, organic or inorganic, solid or liquid carriers suitable for oral or parenteral administration or for topical application may be used, in manufacturing the preparations. Gelatine, lactose, starch magnesium stearate, micronized silica gel, cocoa butter, talc, vegetabilic and animalic fats and oils, vegetabilic rubber and polyalkylene glycol and other known carriers for pharmaceuticals are all suitable for manufacturing preparations of said compounds. Preparations for parenteral use include an ampoule of a sterile solution or suspension with water or other pharmaceutically acceptable liquid as the carrier therefor, or an ampoule of sterile powder for dilution with a pharmaceutically acceptable liquid. The preferred salt of the esters is the hydrochloride, but salts with other inorganic or organic acids, that are also antibiotically active acids, may be used, for instance phosphates, acetates or salts with phenoxymethylpenicillin. Moreover the preparation may contain other pharmaceutically active components, being suitably administratable together with said esters when treating infections diseases, e.g. other suitable antibiotical substances, as well as one or more of ingredients such as diluents, buffers, flavoring agents binders, surface active agents, thickeners, lubricants, preservatives, etc.

An exemplary formulation suitable for tabletting would contain about 75% weight of β,β,β-trichloroethyl 6β-(methoxycarbothio)-6α-chloropenicillanate or t-butyl 7β-(methoxycarbothio)-7α-methoxycephalosporanate, or their salts, e.g., hydrochloride salt, 22.8% by weight of starch or lactose, and 2.2% by weight of magnesium stearate. Oral suspensions might for example, contain about 3.4% by weight of t-butyl 7β-(methoxycarbothio)-7α-methoxycephalosporanate, 5.0% by weight aluminum monostearate, 0.2% by weight of sorbitan monooleate surface active agent, and about 91.48% by weight peanut oil.

In the examples that follow, unless otherwise indicated, the following conditions and procedures apply:

Melting points and boiling points are uncorrected; melting points were determined on a Fisher-John's melting point apparatus. All temperatures are in °C. unless otherwise noted. Nuclear magnetic resonance (NMR) spectra were recorded with a Varian Associates T-60 spectrometer and are reported in parts per million (δ) relative to tetramethylsilane as an internal standard. Infrared spectra (IR) were recorded on a Perkin-Elmer 237 spectraphotometer. High resolution mass spectra were recorded on a CEC-110B High Resolution Mattauch-Herzog Mass Spectrometer. Microanalyses were performed by Galbraith Laboratories, Inc., Knoxville, Tenn. Routine thin layer chromatographs (tlc) were run on Baker-flex silica gel 1B-F TLC sheets. Preparative thick layer chromatographs were performed on EM Reagents precoated silica gel 60 F-254 plates (2 mm thickness). Column chromatographs were performed with either Mallinckrodt silicic acid (100 mesh) or EM Reagents silica gel 60 (finer than 230 mesh).

β,β,β-Trichloroethyl 6-diazopenicillanate was prepared by the method described in J. C. Sheehan, Y. S. Lo, J. Loliger, and C. Podewell, *J. Org. Chem.*, 39, 1444 (1974).

Perchloromethyl mercaptan was obtained from Aldrich Chemical Co., Milwaukee, Wicsonsin, 53233.

Chlorocarbonyl sulfenyl chloride was prepared according to the literature. See, for example, *Chem. Abstr.*, 65 12112h (1966); German Patent 1,224,720.

Carbomethoxy sulfenyl chloride was prepared according to the method described in G. Fumach, and E. Kuhle Angew. Chem., Int. Ed. Engl. 9, 54 (1970).

7-Diazocephalosporanic acid tert-butyl ester was prepared according to the method described in J. S. Wiering and Hans Wynberg, *J. Org. Chem.*, 41, 1474 (1976).

Thiophene-2-acetic acid was obtained from Research Organic/Inorganic Chemical Corp., Belleville, N.J.

Thiophene-2-acetyl chloride was prepared according to the literature. See, for example, *Chem. Abstr.*, 61, 5659 c(1964); U.S. Pat. No. 3,129,224.

Preparation of Benzhydryl 6-Aminopenicillanate

A mixture of 5.400 g (25.0 mmol) of 6-APA and 4.850 g (25.0 mmol) of diphenyldiazomethane in 75 ml of methylene chloride and 25 ml of methanol were stirred at room temperature for 22.5 hr (overnight). At the end of this time the red color was discharged. An additional 2 g of diphenyldiazomethane was added and, after 19 hr, the solid material (6-APA) was removed by filtration and the solution extracted with ice-cold dilute HCl. The organic layer was separated, the aqueous layer extracted 3 times with methylene chloride and then the aqueous layer made basic with $NaHCO_3$. After extraction with methylene chloride and removal of the solvent under reduced pressure (no heat) the benzhydryl ester of 6-APA was isolated as an oil: NMR ($CDCl_3$) δ 1.33 (S, 3H), 1.67 (S, 3H), 1.87 (m, 2H), 4.4–4.17 (m, 2H), 3.87 (d, 1H, J=4.0 Hz), 7.0 (S, 1H), 7.38 (S, 10H).

Preparation of β,β,β-Trichloroethoxycarbonylsulfenyl Chloride

To an ice cold vigorously stirred (mechanical stirrer) solution of trichloroethanol (50.0 ml, 0.52 mol) and pyridine (42.0 ml, 0.52 mol) in 300 ml of methlene chloride, chlorocarbonylsulfenyl chloride (43.5 ml, 0.52 mol) was added dropwise over 30 min. After the addition the solution was stirred at 0° for 1.5 hr. The ice bath was removed and the stirring continued for 1.5 hr. The mixture (solid formed) was washed with ice—H$_2$O and ice cold sat. NaCl. The organic layer was dried (MgSO$_4$) and the solvent removed under reduced pressure. After removal of the solvent an oily solid remained. The solid was removed by triterration with ether and filtration of the solid. The filtrate was condensed under reduced pressure and the process repeated until, after removal of the solvent from the filtrate, the liquid could be filtered without the aid of solvent. The yellow liquid was distilled under reduced pressure: bp 54°–59° (0.25 mm; bath temp. 80°–90°); NMR (CDCl$_3$) δ 5.0 (S, 2H).

Preparation of Benzhydryl 6-diazopenicillanate

Ice water (100 ml), sodium nitrite (232.5 mg, 3.37 mmol) and 3 ml of 1 N HClO$_4$ were added (in that order) to an ice cold solution of the amine in 100 ml of methylene chloride and the mixture vigorously stirred (mechanical stirrer) at 0° for 2 hr. The organic layer was separated, washed with cold sat. NaCl and dried (Na$_2$SO$_4$). Removal of the solvent under reduced pressure (no heat) gave a yellow oil which was dissolved in ether-petroleum ether and after standing at approximately −15° overnight the product crystallized (420 mg, 75%). Recrystallization from ether-petroleum ether gave an analytically pure sample: mp 93.0–94.0; IR (CH$_2$Cl$_2$) 2090, 1760 and 1700 sh; NMR (CDCR$_3$) δ 1.27 (S, 3H), 1.65 (S,3H) 4.47 (S,1H), 6.12 (S,1H), 6.88 (S,1H), 7.30 (S,10H).

Anal. Calcd. for C$_{21}$H$_{19}$N$_3$O$_3$S; C, 64.10; H, 4.87; N, 10.68; S, 8.15. Found C, 64.11; H, 4.90; N, 10.52; S, 8.06.

Preparation of t-Butyl 7-aminocephalosporanate

The tert-butyl ester of 7-aminocephalosporanate was prepared by the method described in E. H. W. Bohme, H. E. Applegate, J. B. Ensing, P. T. Funke, M. S. Puar, and J. E. Dolfini, *J. Org. Chem.*, 38, 230 (1973), and purified in the following manner. After removal of the solvent under reduced pressure (no heat) the crude product (dark brown) was dissolved in methylene chloride and extracted with ice cold dilute HCl. The aqueous layer (kept cold) was extracted with methylene chloride (2 times), partitioned with methylene chloride, and made basic with NaHCO$_3$. After separation of the organic layer, repeated extraction of the aqueous layer with methylene chloride (4 times), drying (MgSO$_4$) and removal of the solvent under reduced pressure (no heat), the product was isolated as a light yellow crystalline material. Recrystallization from methylene chloride (minimum amount)-ether-petroleum ether gave 7-aminocephalosporanic acid tert-butyl ester as a white crystalline product.

General Procedure for Removing Protective Groups

1. Trichloroethyl Group:

The ester (100–200 mg) is dissolved in approx. 10 ml of 90% HOAc and the solution cooled to 0° before 1–1.5 g of zinc dust is added. The mixture is stirred at 0° for 3–5 hr. The removal of the zinc by filtration through celite into a flask containing 100 ml of ice-H$_2$O and washing the zinc with methylene chloride (50 ml) yielded a two-phase system. Separation of the organic layer, extraction of the aqueous layer with several methylene chloride-zinc washings, drying (MgSO$_4$) and removal of the solvent under reduced pressure (no heat) afforded the free acid.

For purification (if required) the acid was dissolved in CH$_2$Cl$_2$ and extracted with aqueous NaHCO$_3$. The aqueous layer, after being extracted several times with CH$_2$Cl$_2$, was cooled with ice and acidified with dilute HCl. Extraction with CH$_2$Cl$_2$, drying (MgSO$_4$) and removal of the solvent under reduced pressure (no heat) gave the pure acid.

2. t-Butyl Group

A flask, charged with the ester, is submerged in an ice bath 5–10 min. before cold trifluoroacetic acid is added. The solution is stirred at 0° for 30–45 min. and then the solvent removed by distillation under reduced pressure (2–3 mm) with the reaction flask still submerged in the ice bath. The residue is freeze dried from benzene.

If purification is required, it is done in the same manner as described for removal of the trichloroethyl group (see above).

3. Benzhydryl Group:

The benzhydryl group is removed in the same manner as described for the removal of the t-butyl group, above. After freeze drying the residue was purified in the following manner. The acid was dissolved in methylene chloride and extracted with aqueous NaHCO$_3$. The aqueous layer, after being extracted several times with methylene chloride, was partitioned with methylene chloride, cooled with ice, and acidified with dilute HCl. Extraction with methylene chloride, drying (MgSO$_4$), and removal of the solvent under reduced pressure (no heat) gave the pure acid.

In order to remove the protective benzhydryl group from benzyhydryl-6β-(triophene-2-acetylthio)-6α-methoxypenicillanate, the following procedure was found necessary. The ester (70–80 mg) is dissolved in 10 ml of CH$_2$Cl$_2$ and the solution cooled to −77° (CO$_2$-acetone) before the addition of 0.5 ml of trifluoroacetic acid. The solution was warmed to approximately −10° (NaCl-H$_2$O-ice) and stirred at that temperature for 5–6 hr. The solution was cooled to −77° and 75–100 ml of benzene added. After the contents of the flask solidified the acid was isolated by freeze drying and bioassayed without purification.

The following examples are provided to further illustrate the present invention.

EXAMPLE 1

Synthesis of β,β,β-Trichloroethyl 6β-(methoxycarbothio)-6α-chloropenicillanate

Carbomethoxysulfenyl chloride (768.8 mg, 6.08 mmol) was added to an ice cold solution of 2.1729 g (6.06 mmol) of the diazo ester in 50 ml of methylene chloride. There was an immediate evolution of gas. The solution was stirred at 0° for 30 min. and then the solvent removed under reduced pressure. The residual oil was chromatographed on silicic acid using methylene chloride as an eluent. Isolation of the fastest moving fraction gave the 6α-chloro ester (2.44 g, 88% as an oil; one spot on tlc): ir (CH$_2$Cl$_2$) 2960, 1790, 1765, sh and 1725 cm$^{-1}$; NMR (CDCl$_3$) δ 1.55 (S, 3H), 1.63 (S,3H), 3.93 (S,3H), 4.68 (S,1H), 4.83 (S, 2H), 5.87 (S, 1H); MS m/e 454.9000 (M+, calcd for C$_{12}$H$_{13}$NO$_5$Cl$_4$S$_2$, 454.8990).

EXAMPLE 2

Synthesis of β,β,β-Trichloroethyl 6β-(methoxycarbothio)-6α-methoxypenicillanate

Carbomethoxysulfenyl chloride (1.0803 g, 8.54 mmol) was added to an ice cold solution of the diazo ester (3.0050 g, 8.38 mmol) in 50 ml of methylene chloride and 50 ml of methanol. There was an immediate evolution of gas. The solution was stirred at 0° for 30 min. and the solvent removed under reduced pressure. The residual oil was chromatographed on silicic acid using methylene chloride as an eluent. Isolation of the fastest moving fraction gave the chloro ester as an oil (132.1 mg, 3%) identical in all respects (nmr, ir, and tlc) to that obtained by treatment of the diazo ester with carbomethoxysulfenyl chloride in the absence of methanol.

Isolation for slower moving fraction gave 28.7 mg of an oil which was subjected to further chromatography on 2-20×20 silica gel plates using methylene chloride—carbon tetrachloride as eluents. Isolation of the most polar fraction gave 18.9 mg (0.5%) of an oil whose spectral data is in complete agreement with the 6β-chloro ester: ir ($CH_2Cl_2$) 2950, 1790, and 1760 $cm^{-1}$; nmr ($CDCl_3$) δ 1.58 (S,3H), 1.83 (S,3H), 3.92 (S,3H), 4.65 (S,1H), 4.78 (S,2H), 5.70 (S, 1H); MS m/e. 395.8868 ($M^+ -59$, calcd for $C_{10}H_{10}NO_3Cl_4S_2$, 395.8856). Isolation of the slowest moving fraction gave 2.97 g (78%) of the 6α-methoxy ester as an oil (one spot on tlc): ir ($CH_2Cl_2$) 2950, 1775, 1755 sh, and 1715 $cm^{-1}$; NMR ($CDCl_3$) δ 1.55 (S,3H), 1.65 (S, 3H), 3.68 (S,3H), 3.88 (S,3H), 4.63 (S,1H), 4.83 (S,2H), 5.68 (S,1H); MS m/e 450.9504 ($M^+$, calcd for $C_{13}H_{16}NO_6Cl_3S_2$, 450.9485).

EXAMPLE 3

Synthesis of Benzhydryl 6β-(β,β,β-trichloroethoxycarbothio)6α-methoxypenicillanate The diazo ester (starting with 2.8354 g, 7.43 mmol of benzhydryl amine in 150 ml of methylene chloride) was prepared as described above. After removal of the $Na_2SO_4$ by filtration the solution was cooled to 0° and 150 ml of methanol added.

β,β,β-Trichloroethoxycarbonylsulfenyl chloride (1.800 g, 7.38 mmol) was added to the above ice cold solution. After stirring at 0° for 15 min. and removal of the solvent under reduced pressure the residual oil was chromatographed on silica gel. (>230 mesh) using methylene chloride as an eluent. Isolation of a minor fraction gave the 6α-chloro ester (54 mg, 1%) identical in all respects (ir, nmr, and tlc) with that obtained from the reaction of the diazo ester with β,β,β-trichloroethoxycarbonylsulfenyl chloride in the absence of methanol.

Isolation of the major fraction gave the 6α-methoxy ester (3.16 g, 70%) as an oil (1 spot on tlc) as the only other β-lactam component: ir ($CH_2Cl_2$) 1775 and 1740 $cm^{-1}$; NMR ($CDCl_3$) δ 1.28 (S, 3H), 1.60 (S,3H), 3.68 (S,3H), 4.60 (S,1H), 4.85 (S,2H), 5.70 (S,1H), 6.92 (S, 1H), 7.33 (S,10H); MS m/e 603.0130 ($M^+$, calcd for $C_{25}H_{24}NO_6Cl_3S_2$, 603.0111).

EXAMPLE 4

Synthesis of Benzhydryl 6β-mercapto-6α-methoxypenicillanate

The 6α-methoxy ester of Example 3 (1.2346 g, 2.04 mmol) was dissolved in 30 ml of 90% HOAc and the solution cooled to 0° before 1.6 g of zinc dust was added. The mixture was stirred at 0° for 5 hr. Removal of the zinc by filtration through celite into a flask containing ice water and washing of the zinc with methylene chloride gave a two phase system. The aqueous layer was made basic with $NaHCO_3$ and extracted with the organic layer. Separation of the organic layer, extraction of the aqueous layer with several methylene chloride—zinc washings, drying ($MgSO_4$) and removal of the solvent under reduced pressure (no heat) gave the mercaptan as a crystalline product in quantitative yield. Recrystallization from methylene chloride—petroleum ether gave an analytically pure sample: mp 127.5-129.-0;ir ($CH_2Cl_2$) 3030, 2950, 1775 and 1740 $cm^{-1}$; NMR ($CDCl_3$) δ 1.30 (S 3H), 1.67 (S,3H), 2.55 (S, 1H), 3.50 (S, 3H), 4.55 (S, 1H), 5.40 (S, 1H), 6.85 (S, 1H), 7.25 (S, 10H).

Anal. Calcd for $C_{22}H_{23}NO_4S_2$: C, 61.52; H, 5.40; N, 3.26; s, 14.93. Found: C, 61.58; H, 5.41; N, 3.23; S, 14.93.

EXAMPLE 5

Synthesis of Benzhydryl 6β-(phenylacetylthio)-6α-methoxypenicillanate

A solution of 397.8 mg (9.26mmol) of the mercaptan of Example 4 in 20 ml of methylene chloride was cooled to 0° before 122 μl (9.22 mmol) of phenylacetyl chloride and 75 μl (9.27 mmol) of pyridine were added. The solution was stirred at 0° for 3 hr. and then extracted with ice cold dilute HCl, aqueous $NaHCO_3$, dried ($MgSO_4$) and the solvent removed under reduced pressure. After chromatography on silica gel 60 (>230 mesh) using methylene chloride as an eluent the 6α-methoxy ester (389 mg, 77%) was isolated as an oil: ir ($CH_2Cl_2$) 3050, 2925, 1770, 1740 and 1705 $cm^{-1}$; NMR ($CDCl_3$) 1.22 (S,3H), 1.45 (S,3H), 3.50 (S,3H), 3.78 (S,2H), 4.45 (S,1H), 5.63 (S,1H), 6.77 (S,1H), 6.9–7.3 (m,15H).

EXAMPLE 6

Synthesis of tert-Butyl 7β-(methoxycarbothio)-7-methoxycephalosporanate

A vigorously stirred (mechanical stirrer) solution of tert-butyl cephalosporanate (1.0082 g, 3.05 mmol) in 100 ml of $CH_2Cl_2$ was cooled to 0° before 100 ml of ice-$H_2O$, 9.00 g. (0.13 mol) of sodium nitrite and 574.7 mg (3.02 mmol) of p-TsOH-$H_2O$ (p-toluene sulfonic acid-water) were added in that order. After 5 min. a total of 833.2 mg (4.38 mmol) more p-TsOH-$H_2O$ was added gradually over 45 min. After the last addition the mixture was stirred at 0° for 15 min. and then the organic layer separated (kept cold), washed 2 times with cold sat. NaCl. dried ($MgSO_4$) and the solution condensed under reduced pressure (no heat) to a volume of approx. 20 ml.

The above solution was cooled to 0° and 20 ml of anhydrous MeOH added. Carbomethoxysulfenyl chloride (310.3 mg, 2.42 mmol; 0.8 mol based on 7-ACA-tert-butyl ester) was added to the ice cold solution and there was an immediate evolution of gas. The solution was stirred at 0° for 45 min. and the solvent removed under reduced pressure. The residual oil was chromotographed on silicic acid using 40:1 $CH_2Cl_2$: ether as an eluent. Isolation of a fast moving fraction gave the α and β-chloroesters as a mixture (96.4 mg of oil, 7%): NMR ($CDCl_3$) δ 1.67 (18H), 2.17 (S,6H), 3.2–3.6 (m,4H), 5.28 (S,1H), 3.97 (S,3H), 4.2–5.4 (m,4H), 5.18 (S,1H), 5.28 (S, 1H).

Isolation of a slower moving fraction gave the 7β-methoxy ester as an oil (76.9 mg, 6%): NMR ($CDCl_3$) δ 1.63 (S,9H), 2.17 (S,3H), 3.3–3.7 (M,2H), 3.73 (S,3H), 3.93 (S,3H), 4.6–5.3 (m,2H), 5.23 (s,1H).

Isolation of the slowest moving fraction gave the 7α-methoxy ester as an oil (320.8 mg, 24%): ir (CH$_2$CH$_2$) 2950, 1775 and 1725 cm$^{-1}$; NMR (CDCl$_3$) δ 1.65 (S,9H), 2.15 (S,3H), 3.3–3.6 (m,2H), 3.72 (S,3H) 3.90 (S,3H), 4.18–5.3 (m,2H), 5.07 (S,1H).

EXAMPLE 7

Synthesis of tert-Butyl 7β-β,β,β-trichloroethoxycarbothio)-7α-methoxycephalosporanate A vigorously stirred (mechanical stirrer) solution of tert-butyl 7-aminocephalosporanate (2.000 g, 6.10 mmol,) in 200 ml of methylene chloride was cooled to 0° before 200 ml of ice water, 18.000 g (0.261 mmol) of sodium nitrite and 1.150 g (6.04 mmol) of p-TsOH-H$_2$O were added in that order. After 5 min. a total of 1.66 g (8.73 mmol) of p-TsOH was added gradually over 40 min. After the last addition the mixture was stirred at 0° for 10 min. and then the organic layer separated (kept cold), washed with cold sat NaCl, and dried (Na$_2$SO$_4$). The Na$_2$SO$_4$ was removed by filtration and the filtrate (approx. 400 ml) cooled to 0° before 100 ml of methanol and 1.20 g (4.92 mmol; 0.8 equivalents bases on starting amine) of β,β,β-trichloroethoxycarbonylsulfenyl chloride were added in that order. The solution was stirred at 0° for 30 min. and then the solvent removed under reduced pressure. The residual oil was chromatographed on silica gel 60 (>230 mesh) using 100:1 methylene chloride:ether (v/v) as an eluent. Isolation of the least polar β-lactam fraction gave the α and β chloroesters as a mixture (43 mg of oil, 1%) identical in all respects (ir, nmr and tlc) to the mixture (vide infra) obtained by treatment of the diazo ester with β,β,β-trichloroethoxycarbonylsulfenyl chloride in the absence of methanol.

Isolation of a slower moving fraction gave the 7β-methoxy ester as an oil which crystallized on standing (232 mg, 7%). Recrystallization from methylene chloride-petroleum ether gave an analytically pure sample: mp 95°–97°; ir (CH$_2$Cl$_2$) 2970, 1780 and 1725 cm$^{-1}$; NMR (CDCl$_3$) δ 1.63 (S,9H), 2.15 (S,3H), 3.32 (d,1H), J=18.0 Hz) 3.63 (d,1H, J=18.0 Hz), 3.72 (S,3H), 4.7–5.3 (m,5H); C-6 proton singlet at 5.15).

Anal. Calcd. for C$_{18}$H$_{22}$NO$_8$S$_2$Cl$_3$: C, 39.25; H, 4.03; N, 2.54; Cl. 19.31; S, 11.64. Found: C, 39.19; H, 4.11; N, 2.48; Cl, 19.29; S, 11.85.

Isolation of the slowest moving fraction gave the 7α-methoxy ester as an oil which crystallized on standing (1.18 g, 35%). Recrystallization from methylene chloride-petroleum ether gave an analytically pure sample; mp 85.0–87.5; ir (CH$_2$Cl$_2$) 2950, 1775 and 1735 cm$^{-1}$; NMR (CDCl$_3$) δ 1.57 (S,9H), 2.10 (S,3H), 3.25 (d,1H, J=18.0 Hz), 3.62 (d, 1H, J=18.0 Hz) 3.73 (S, 3H), 4.6–5.3 (m,5H); C-6 proton singlet at 5.10).

Anal. Calcd. for C$_{18}$H$_{22}$NO$_8$S$_2$Cl$_3$: C, 39.25; H, 4.03; N, 2.54; Cl, 19.31; S, 11.64. Found: C, 39.41; H, 4.16; N, 2.45; Cl, 19.44; S, 11.76.

EXAMPLE 8

Synthesis of tert-Butyl 7β-mercapto-7α-methoxycephalosporanate

The α-methoxy ester (192.7 mg) of Example 7 dissolved in 10 ml of 90% HOAc and the solution cooled to 0° before 1.1738 g of zinc dust was added. The solution was stirred at 0° for 5 hr. Removal of the zinc by filtration through celite into a flask containing ice-H$_2$O and washing of the zinc with methylene chloride gave a two-phase system. The aqueous layer was made basic with NaHCO$_3$ and extracted with several methylene chloride—zinc washings, drying (MgSO$_4$) and removal of the solvent under reduced pressure (no heat) gave the mercaptan as an unstable oil: ir (CH$_2$Cl$_2$) 2950 sh, 2920, 1775, and 1725 cm$^{-1}$; NMR (CDCl$_3$) δ 1.58 (S, 9H), 2.10 (S, 3H), 2.55 (S, 1H), 3.30 (d, 1H, J=18.0 Hz), 3.60 (d, 1H, J=18.0 Hz), 3.60 (S,3H), 4.82 (d, 1H, J=13.0 Hz), 4.88 (S, 1H), 5.13 (d, 1H, J=13.0 Hz).

EXAMPLE 9

Synthesis of tert-Butyl 7β-(phenoxyacetylthio)-7α-methoxycephalosporanate

In the same manner as described above the mercaptan of Example 8 was isolated as an oil and used immediately in the following reaction.

A solution of 270.4 mg. (0.720 mmol) of the mercaptan (crude product) in 20 ml of CH$_2$Cl$_2$ was cooled to 0° before 60 μl (0.776 mmol) of pyridine and 125.5 mg (0.736 mmol) of phenoxyacetyl chloride were added in that order. The solution was stirred at 0° for 1.5 hr. and then extracted with ice-cold dilute HCl, aqueous NaHCO$_3$, dried (MgSO$_4$) and the solvent removed under reduced pressure. After chromatography on silica gel 60 (>230 mesh) the 7α-methoxy ester was isolated as an oil: ir (CH$_2$Cl$_2$) 2930, 1775, 1740 sh, and 1720 cm$^{-1}$; NMR (CDCl$_3$) δ 1.63 (S, 9H), 2.13 (S, 3H), 3.17 (d, 1H, J=18.0 Hz), 3.57 (d, 1H, J=18.0 Hz), 3.63 (s, 3H), 4.6–5.3 (m,2H), 4.73 (S, 2H), 5.13 (S, 1H), 6.7–7.5 (m, 5H).

EXAMPLE 10

Synthesis of tert-Butyl 7β-(phenylacetylthio)-7α-methoxycephalosporanate (21)

In the same manner as described above the mercaptan of Example 8 was isolated as an oil and used immediately in the following reaction.

A solution of 239 mg. (0.637 mmol) of the mercaptan in 10 ml of methylene chloride was cooled to 0° before 52 μl (0.643 mmol) of pyridine and 84 μl (0.635) of phenylacetyl chloride were added in that order. The solution was stirred at 0° for 2.75 hr. and then extracted with ice cold dilute HCl, aqueous NaHCO$_3$, dried (MgSO$_4$) and the solvent removed under reduced pressure. After chromatography on silica gel 60 (>230 mesh) using 50:1 methylene chloride-ether (v/v) as an eluent the 7α-methoxy ester was isolated as an oil (184 mg, 59%) which crystallized on standing. Recrystallization from ether-petroleum ether gave an analytically pure sample: mp 78°–80°; ir (CH$_2$Cl$_2$) 2950, 1775, 1735 sh and 1720 cm$^{-1}$; NMR (CDCl$_3$) δ 1.62 (S, 9H), 2.13 (S, 3H), 3.20 (d, 1H, J=18.0 Hz), 3.60 (d, 1H, J=18.0 Hz), 3.62 (S, 3H) 3.92 (S, 2H), 4.77 (d, 1H, J=14.0 Hz), 5.08 (d, 1H, J=14.0 Hz), 5.10 (S, 1H), 7.30 (S, 5H).

Anal. Calcd. for C$_{23}$H$_{27}$NO$_7$S$_2$: C, 55.97; H, 5.51; N, 2.84; S, 12.99. Found: C, 56.12; H, 5.48; N, 2.78; S, 12.99.

EXAMPLE 11

Synthesis of tert-Butyl 7β-(thiophene-2-acetylthio)-7α-methoxycephalosporanate

In the same manner as described for Example 10, t-butyl 7β-(thiophene-2-acetylthio)-7α-methoxycephalosporanate was prepared except thiophene-2-acetyl chloride was used in place of phenylacetyl chloride. The 7-methoxy ester was isolated as an oil (206 mg, 68%) which crystallized on standing. Recrystallization from ether-petroleum ether gave an analytically pure sample: mp 78°-80°; ir (CH$_2$Cl$_2$) 2950, 1775, 1735 sh and 1720 cm$^{-1}$; NMR (CDCl$_3$) δ1.62 (S, 9H), 2.10 (S, 3H), 3.15 (d, 1H, J=17.0 Hz), 3.53 (d, 1H, J=17.0 Hz), 3.60 (S, 3H), 3.73 (S, 2H), 4.70 (d, 1H, J=13.0 Hz), 5.00 (d, 1H, J=13.0 Hz), 5.03 (S, 1H), 6.8-7.4 (m, 3H).

Anal.Calcd. for C$_{21}$H$_{25}$NO$_7$S$_3$: C, 50.58; H, 5.03; N, 2.80; S, 19.21. Found: C, 50.62; H, 5.20; N, 2.75; S, 19.31.

EXAMPLE 12

Synthesis of β,β,β-Trichloroethyl 7β-(methoxycarbothio)-7α-methoxydeacetoxycephalosporante A solution of m-chloroperbenzoic acid (393.2 mg, 2.27 mmol) in 20 ml of chloroform was added dropwise over 45 min. to an ice cold solution of β,β,β-trichloroethyl-6β-methoxycarbothio-6α-methoxypenicillanate (1.0256 g, 2.27 mmol) in 50 ml of chloroform. After the addition the stirring was continued at 0° for an hr., extracted with aqueous NaHCO$_3$, dried and the solvent removed under reduced pressure. The residual oil (503.4 mg of residual oil) was dissolved in 32 ml of dry benzene. N,N-Dimethylacetamide (24 ml) and 3 drops of methanesulfonic acid were added and the mixture refluxed under a Dean-Stark trap, protected from moisture with a drying tube, for 20.5 hr. (temperature of external heating bath maintained at 114°-120°). Removal of the solvent by distillation (temperature of heating bath approx. 55°; 2-3 mm Hg) and chromatography of the residual oil on silicic acid using 50:1 CH$_2$Cl$_2$: ether as an eluent gave the 7α-methoxy ester as an oil which crystallized from ether-petroleum ether (59%). ir (CH Cl) 2945, 1775, and 1725 cm; NMR (ClCl) 2.30 (S, 3H), 2.8-3.5 (m, 2H), 3.65 (s, 3H), 3.83 (S, 3H), 4.82 (S, 2H), 5.07 (S, 1H).

EXAMPLE 13

Synthesis of Benzhydryl 6β-(β,β,β-trichloroethoxycarbothio)-6α-chloropenicillanate The diazo ester of 6-APA was prepared as described above. After removal of the Na$_2$SO$_4$ by filtration the methylene chloride solution of the diazo ester was cooled to 0° and used in the following reaction.

β,β,β-Trichloroethoxycarbonylsulfenyl chloride (243.8 mg, 5.00 mmol; 1 equivalent based on starting benzhydryl amine) was added to the above ice cold solution of the diazo ester. The solution was stirred at 0° for approximately 30 min. and then the solvent removed under reduced pressure. The residual oil was chromatographed on silica gel 60 (>230 mesh) using methylene chloride as an eluent. Isolation of the major fraction gave the 6α-chloro ester (593 mg, 20%; oil) as the only identifiable β-lactam component: ir (CH$_2$Cl$_2$) 3040, 2950, 1790 and 1740 cm$^{-1}$; NMR (CDCl$_3$) δ1.28 (S, 3H), 1.60 (S, 3H), 4.58 (S, 1H), 4.73 (d, 1H, J=10.0 Hz), 4.93 (d, 1H, J=10.0 Hz), 5.80 (S, 1H), 6.83 (s, 1H), 7.23 (S, 10H).

EXAMPLE 14

Synthesis of Benzhydryl 6β-(thiophene-2-acetylthio)-6α-methoxypenicillanate

In the same manner as described in Example 5, benzhydryl 6α-(thiophene-2-acetylthio)-6α-methoxypenicillanate was prepared except that thiophene-2-acetyl chloride was used in place of phenylacetyl chloride.

The 6α-methoxy ester was isolated as an oil (83%) after chromatography on silica gel 60 (>230 mesh) using methylene chloride as an eluent: ir (CH$_2$Cl$_2$) 3050, 2960, 1775 1740, and 1705 cm$^{-1}$; NMR (CDCl$_3$) δ1.23 (S, 3H), 1.48 (S, 3H), 3.53 (S, 3H), 3.98 (S, 2H), 4.48 (S, 1H), 5.70 (S, 1H), 6.7-7.5 (m, 14H).

EXAMPLE 15

Synthesis of tert-Butyl 7β-(β,β,β-trichloroethoxycarbothio)-7α-chlorocephalosporanates A vigorous stirred (mechanical stirrer) solution of tert-butyl 7-aminocephalosporanate (2.000 g, 6.10 mmol) in 200 ml of methylene chloride was cooled to 0° before 200 ml of ice water, 18.000 g (0.261 mmol) of sodium nitrate and 1.150 g (6.04 mmol) of p-TsOH-H$_2$O were added in that order. After 5 min. a total of 1.660 g (8.73 mmol) of p-TsOH-H$_2$O was added gradually over 40 min. After the last addition the mixture was stirred at 0° for 15 min. and then the organic layer separated (kept cold), washed with cold sat. NaCl, and dried (Na$_2$SO$_4$). The Na$_2$SO$_4$ was removed by filtration and the filtrate cooled to 0° before the addition of 1.20 g (4.92 mmol; 0.8 equivalents based on starting amine) of β, β,β-trichloroethoxycarbonylsulfenyl chloride. The solution was stirred at 0° for 15 min. and then the solvent removed under reduced pressure and the residual oil chromatographed on silica gel 60 (>230 mesh) using 100:1 methylene chloride: ether (v/v) as an eluent. The chloro esters (365 mg of oil, 11%) were isolated as a mixture of isomers in a ratio of approximately 2:1 by nmr integration of the C-6 protons: ir (CH$_2$Cl$_2$) 2950, 1790 and 1735 cm$^{-1}$; NMR (CDCl$_3$) δ1.63 (S, 1H), 2.15 (S, 6H), 3.3-3.7 (m, 4H), 4.7-5.4 (m, 10H; C-6 protons are singlets at 5.17 and 5.27 in a ratio of 1:2 respectively).

The mixture of chloro esters (254 mg) was chromatographed on 100 g of silica gel 60 (230 mesh; dried at 125° for 12 hr. prior to use) using 200:1 methylene chloride: ether (v/v) as an eluent. Fractions collected were monitored by nmr analysis. Three fractions were collected. The middle fraction was a mixture of isomers.

Less polar fraction (20 mg of oil): ir (CH$_2$Cl$_2$) 2925, 1790, and 1735 cm$^{-1}$; NMR (CDCl$_3$) δ1.57 (S, 9H), 2.10 (S, 3H), 3.2-3.6 (m, 2H), 4.5-5.3 (m, 5H, C-6 proton singlet at 5.17).

More polar isomer (32 mg of oil): ir (CH$_2$Cl$_2$) 2950, 1790 and 1735 cm$^{-1}$NMR (CDCl$_3$) δ1.60 (S, 9H), 2.12 (S, 3H), 3.22 (d, 1H, J=18.0 Hz), 3.55 (d, 1H, J=18.0 Hz), 4.6-5.4 (m, 5H; C-6 proton singlet at 5.27).

EXAMPLE 16

The protective groups of the penicillin and cephalosporin esters were removed as described above and the resulting free acids were tested in vitro for bioactivity. The minimum inhibitory concentration values for various bacteria are given in Table I below.

TABLE 1

Minimum Inhibitory Concentration for Certain Penicillin and Cephalosporin Esters
Minimum Inhibitory Concentration, mg/ml

| Ester | Bacillus subtillis ATCC 6051 | Sarcina lutea | Staphylococcus aerus (Roche) |
|---|---|---|---|
| β,β,β-Trichloroethyl 6β-methoxycarbothio) - 6αchloro- | 100 | 100 | — |

TABLE 1-continued

Minimum Inhibitory Concentration for Certain Penicillin and Cephalosporin Esters

| Ester | Minimum Inhibitory Concentration, mg/ml | | |
|---|---|---|---|
| | Bacillus subtillis ATCC 6051 | Sarcina lutea | Staphylococcus aerus (Roche) |
| penicillanate Benzhydryl 6β-(β,β,β-trichloro-ethoxycarbothio)-6α-methoxy-penicillanate | 100 | — | — |
| t-Butyl 7β-(methoxycarbothio)-7α-methoxycephalosporanate | 50 | 25 | 50 |
| t-Butyl 7β-(phenylacetylthio)-7α-methoxycephalosporanate | <6.25 | 100 | — |
| t-Butyl 7β-(thiophene-2-acetylthio)-7α-methoxycephalosporanate | 50 | — | — |

While the invention and its preferred embodiments have been described and illustrated herein, many modificaions and extensions within the spirit and scope of the invention will be apparent to those skilled in the art. Such modifications and extensions are considered and intended to be within the scope and spirit of the appended claims.

We claim:

1. A compound having the formula:

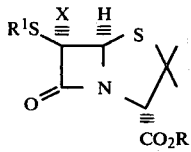

where R is a protective group for acids or a pharmaceutically acceptable group, $R^1$ is hydrogen or an organic electrophilic moiety, and X is a halogen or an organic nucleophile.

2. The compound of claim 1 wherein R is selected from the group consisting of hydrogen, an aliphatic group, an alicyclic group, an aromatic group, an alkali metal salt, a quaternary ammonium group, an organosilyl group, and an acyl group.

3. The compound of claim 1 wherein R is selected from the group consisting of alkyl groups, alkenyl groups, alkinyl groups, cycloalkyl groups, cycloalkenyl groups, aryl groups, aralkyl groups, alkaryl groups, acyl groups, acylamino groups, acylaminoalkyl groups, imino groups and arylacyl groups.

4. The compound of claim 1 wherein R is selected from the group consisting of a t-butyl group, a β,β,β-trichloroethyl group, a phenacyl group, a benzyl group, a benzhydryl group, trialkylsilyl group and a alkali metal ion.

5. The compound of claim 1 wherein $R^1$ is selected from the group consisting of aliphatic moieties, alicyclic moieties, aromatic moieties, carboxylic moeities, carbonic moieties, sulonic moieites and amide moieties.

6. The compound of claim 1 wherein $R^1$ is selected from the group consisting of hydrogen, formyl, acetyl, phenyl, phenylacetyl phenoxyacetyl, p-aminophenylacetyl, α-carboxylphenylacetyl, benzyl, benzoyl, 2-thienylacetyl, aminocarbamyl, phenylglycyl, methylsulfonyl, benzylsulfonyl, o-aminophenylsulfonyl, p-aminobenzylsulfonyl, carbobenzoxy, α-carbonaphthoxy, β,β,β-trichloroethoxycarbo carbo (2-thienylmethoxy) and (1-phenyl-2-formylamino)ethoxycarbonyl.

7. The compound of claim 1 wherein X is selected from the group consisting of halogen, an aliphatic moiety, an alicyclic moiety, and an aromatic moiety.

8. The compound of claim 1 wherein X is selected from the group consisting of halogen and alkoxy moieties.

9. The compound of claim 1 wherein R is selected from the group consisting of a t-butyl group, a β,β,β-trichloroethyl group, a phenacyl group, a benzyl group, a benzhydryl group, trialkylsilyl group and a alkali metal ion; $R^1$ is selected from the group consisting of hydrogen, formyl, acetyl, phenyl, phenylacetyl, phenoxyacetyl, p-aminophenylacetyl, α-carboxylphenylacetyl, benzyl, benzoyl, 2-thienylacetyl, aminocarbamyl, phenylglycyl, methylsulfonyl, benzylsulfonyl, o-aminophenylsulfonyl, p-amino-benzylsulfonyl, carbobenzoxy, α-carbonaphthoxy, carbo(2-thienylmethoxy) and (1-phenyl-2-formylamino)ethoxycarbonyl; and X is selected from the group consisting of halogen and alkoxy moieities.

10. The compound of claim 1 wherein R is β,β,β-trichloroethyl, $R^1$ is methoxycarbo and X is chloro.

11. The compound of claim 1 wherein R is benzhydryl, $R^1$ is β,β,β-trichloroethoxycarbo and X is methoxy.

12. The compound of claim 1 wherein said compound is selected from the group consisting of:

β,β,β-Trichloroethyl 6β-(methoxycarbothio)-6α-chloropenicillanate;

β,β,β-Trichloroethyl 6β-(methoxycarbothio)-6α-methoxypenicillanate;

Benzhydryl 6β-(β,β,β-Trichloroethoxycarbothio)-6α-methoxypenicillanate;

Benzhydryl 6β-mercapto-6β-methoxypenicillanate;

Benzhydryl 6β-(β,β,β-trichloroethoxycarbothio)-6α-chloropenicillanate; and

Benzhydryl 6β-(thiophene-2-acetylthio)-6α-methoxypenicillanate.

13. A method for making a penicillanic compound having the formula:

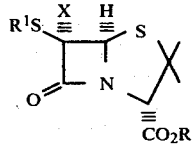

where R is a protective group for acids or a pharmaceutically acceptable group, $R^1$ is hydrogen or an organic electrophilic moiety, and X is a halogen or an organic nucleophile, said method comprising treating a 6-diazopenicillanate having the formula

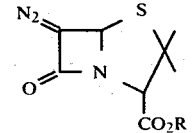

where R is the same as above with a sulfenyl halide by itself or in the presence of a halogen or an organic nucleophile.

14. The method for making a penicillanic compound as described in claim 13 wherein $R^1$ is a carbonyl group and said method further includes removing said carbonyl group to form a mercaptan.

15. The method for making a penicillanic compound as described in claim 14 wherein $R^1$ is selected from the group consisting of chloracetyl, bromoacetyl, ethoxyacetyl, nitrobenzoyl, dimethoxylmethyl, $\beta,\beta,\beta$-trichloroethoxycarbonyl and phenoxyacetyl groups.

16. The method for making a penicillanic compound as described in claim 13 wherein said method includes removing R to form the corresponding free acid.

17. A method for making a penicillanic compound having the formula:

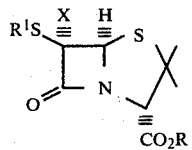

where R is a protective group for acids or a pharmaceutically acceptable group, $R^1$ is hydrogen or an organic electrophilic moiety, and X is a halogen or an organic nucleophile, said method comprising the steps of:

forming a 6-diazopenicillanate having the formula:

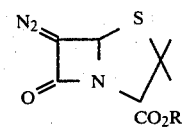

where R is the same as above, and reacting said 6-diazopenicillanate with a sulfenyl chloride by itself or in the presence of a halogen or an organic nucleophile, thus forming said penicillanic compound.

18. The method for making a penicillanic compound as described in claim 17 wherein said sulfenyl chloride comprises a moeity selected from the group consisting of formyl, acetyl, phenyl, phenylacetyl, phenoxyacetyl, p-aminophenylacetyl, α-carboxylphenylacetyl, benzyl, benzoyl, 2 thienylacetyl, aminocarbamyl, phenyglycyl, methylsulfonyl, benzylsulfonyl, o-aminophenylsulfonyl, p-aminobenzylsulfonyl, carbobenzoxy, α-carbonaphthoxy, carbo(2-thienylmethoxy) and (1-phenyl-2-formylamino)ethoxycarbonyl and $\beta,\beta,\beta$-trichloroethoxycarbonyl.

19. The method for making a penicillanic compound as described in claim 13, said method further comprising removing the acid protective group R from said compound and substituting therefor a substituent selected from the group consistig of hydrogen, alkali metal ions, quarternary ammonium ions, and substituted and unsubstituted aliphatic, alicyclic, aromatic, acyl, and organosilyl groups.

20. The method of claim 19 wherein said removing step is effected by treating with zinc-acetic acid.

21. The method of claim 19 wherein said step of removing is characterized by hydrogenation.

22. The method for making a penicillanic compound as described in claim 13, said method further comprising removing said organic electrophile from said compound and substituting therefor a substituent selected from the group consisting of hydrogen, and substituted and unsubstituted aliphatic, alicyclic, aromatic, carboxylic, carbonyl, sulfonic, and amide groups.

23. A sulfoxide compound useful for making cephalosporanic compounds having a nucleophile substituted at the 7- position, said sulfoxide having the formula:

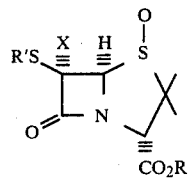

wherein R is a protective group for acids or a pharmaceutically acceptable group, $R_1$ is hydrogen or an organic electrophilic moiety, and X is a halogen or an organic nucleophile.

24. The sulfoxide compound of claim 23 wherein R is selected from the group consisting of hydrogen; substituted or unsubstituted aliphatic, alicyclic, aromatic, acyl and organosilyl groups; alkali metal ions and quaternary ammonium ions.

25. The sulfoxide compound of claim 23 wherein $R^1$ is selected from the group consisting of hydrogen, and substituted or unsubstituted aliphatic, alicyclic, aromatic, carboxylic, carbonic, sulfonic and amide groups.

26. A antibacterial pharmaceutical composition, comprising a material selected from the group consisting of
(1) a penicillanic compound having the structural formula:

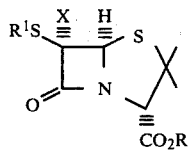

wherein R is a pharmaceutically acceptable substituent selected from the group of hydrogen; substituted or unsubstituted aliphatic, alicyclic, aromatic, acyl, and organosilyl groups; alkali metal ions, and quaternary ammonium ions; $R^1$ is an organic electrophile selected from the group of substituted or unsubstituted aliphatic, alicyclic, aromatic, carboxylic, carbonic, sulfonic and amide radicals; and X is a nucleophile;
(2) pharmaceutically acceptable salts of said penicillanic compounds; and a pharmaceutically acceptable carrier therefor.

27. A method of treating a bacterial infection in a mammal, comprising administering to the mammal an effective amount of the composition of claim 26.

28. A process for preparing a antibacterial pharmaceutical composition, comprising mixing a material selected from the group consisting of
(1) a penicillanic compound having the structural formula:

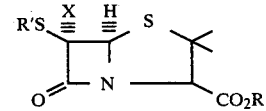

wherein R is a pharmaceutically acceptable substituent selected from the group of hydrogen; substituted or unsubstituted aliphatic, alicyclic, aromatic, acyl, and organosilyl groups; alkali metal ions, and quaternary ammonium ions; $R^1$ is an organic electrophile selected from the group consisting of substituted or unsubstituted aliphatic, alicyclic, aromatic, carboxylic, carbonic, sulfonic, and amide groups; and X is halogen or an organic nucleophile;
(2) pharmaceutically acceptable salts of said penicillanic compounds with a pharmaceutically acceptable carrier therefor.

* * * * *